United States Patent [19]

Hachey

[11] Patent Number: 4,763,065
[45] Date of Patent: Aug. 9, 1988

[54] APPARATUS FOR THE DETECTION AND MEASUREMENT OF SUSPENDED PARTICULATES IN A MOLTEN METAL

[75] Inventor: Raynald Hachey, Shipshaw, Canada

[73] Assignee: Alcan International Limited, Montreal, Canada

[21] Appl. No.: 741,458

[22] Filed: Jun. 5, 1985

[30] Foreign Application Priority Data

Jun. 11, 1984 [GB] United Kingdom ............. 8414856

[51] Int. Cl.$^4$ .................. G01N 27/07; G01R 27/22
[52] U.S. Cl. .................... 324/71.4; 164/4.1; 266/99; 324/65 R
[58] Field of Search ........... 324/71.1, 71.4, 65 R; 164/4.1; 266/99; 73/865.5

[56] References Cited

U.S. PATENT DOCUMENTS

| | | | |
|---|---|---|---|
| 3,361,965 | 1/1968 | Coulter et al. | 324/71.1 |
| 3,395,343 | 7/1968 | Morgan et al. | 324/71.1 |
| 3,714,565 | 1/1973 | Coulter et al. | 324/71.1 |
| 4,555,662 | 11/1985 | Doutre et al. | 324/71.4 |

Primary Examiner—Gerard R. Strecker
Attorney, Agent, or Firm—Cooper & Dunham

[57] ABSTRACT

An apparatus and method for the detection and measurement in a molten metal sample of suspended particulates comprises a container having a composite wall including concentric electrically conducting outer and inner walls (10) and (12) and a disc (14) of refractory material having a passage (16) of predetermined size therethrough providing communication between the inside and outside of the container. In use, molten metal is pumped through the passage (16) so as to establish a current path from the inner wall through the passage to the out wall. A current is passed along the current path, and voltage changes are measured as indicating passage of suspended particulates through the passage.

8 Claims, 1 Drawing Sheet

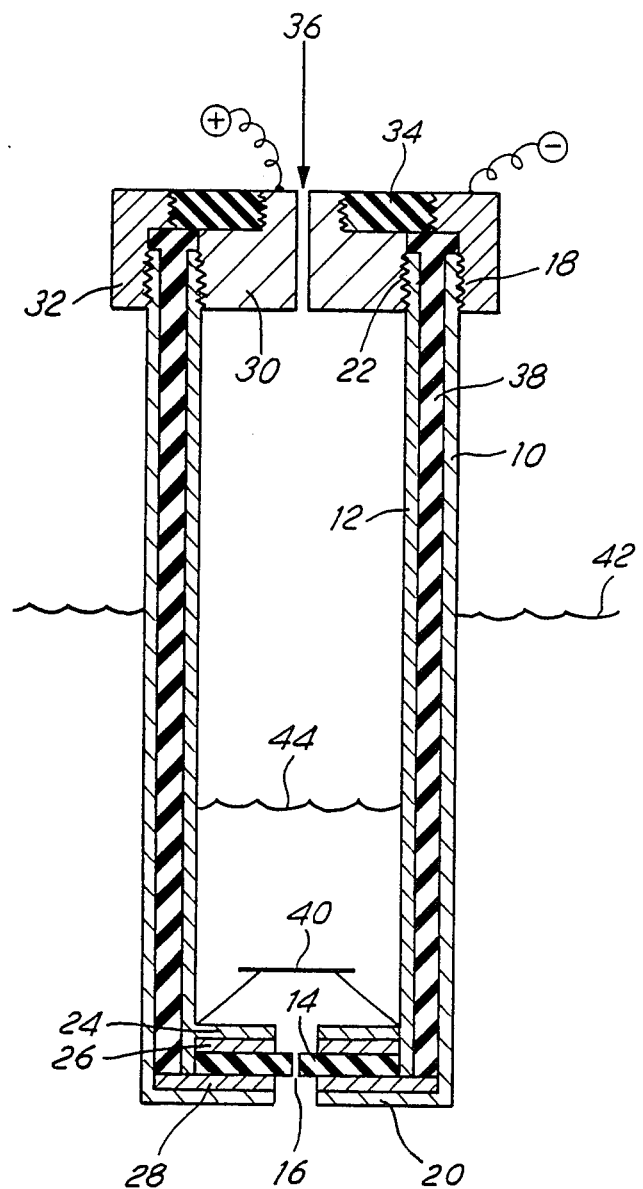

APPARATUS FOR THE DETECTION AND MEASUREMENT OF SUSPENDED PARTICULATES IN A MOLTEN METAL

U.S. Pat. No. 4,555,662 describes a method and apparatus for the detection and measurement in molten metal sample of suspended particulates of greater than a predetermined size whose electrical conductivity differ from that of the suspending molten metal. The apparatus comprises an electrically insulating wall having a small passage (typically 200 to 500 microns diameter) therethrough; a pair of electrodes disposed on opposite sides of the wall to establish a current path between them through the molten metal of the sample and passing through the passage; means for passing a sample of molten metal through the passage; and means for passing an electric current between the two electrodes through the molten metal in the current path and for detecting a change of voltage in the path resulting from the passage through the passage of the said particulates. The apparatus also includes means for counting the number of voltage changes as representative of the number of particulates, and for measuring the sizes of the changes as representtative of the size of the particulates causing the changes. The device described comprises a refractory tube with the small hole at its lower end, which is dipped in the molten metal, for example in a trough along which the molten metal is flowing. One electrode is positioned within the tube and the other outside it. Molten metal is caused to pass through the small hole by means of a differential pressure applied to the tube.

Although this device works well in practice, it is subject to a few disadvantages. The tube needs to be made of an electrically insulating refractory material. If glass is used, there is an upper limit of about 725° C. to the temperatures that can be tolerated. Moreover refractory materials are expensive, and easily broken, and difficult to machine accurately enough to provide a small hole of predetermined size. The tube is comparatively weak, thus placing a limit on the differential pressure that can be applied within it. Separate electrodes have to be provided, both inside and outside the tube; this is inconvenient, and the length and position of the electrodes may affect the results obtained.

It is an object of the present invention to overcome these disadvantages.

The present invention provides apparatus for the detection and measurement in a molten metal sample of suspended particulates comprising
 a container having a composite wall including an electrically conducting outer wall and an electrically conducting inner wall, the inner wall and outer wall being electrically insulated from one another, and an electrically insulating barrier including a passage of predetermined size therethrough providing communication between the inside and outside of the container,
 means for causing a sample of molten metal to pass through the passage into (or out of) the container so that molten metal in the container is in electrical contact with the inner wall and molten metal outside the container is in electrical contact with the outer wall, establishing a current path from the inner wall through the passage to the outer wall,
 and means for passing an electric current along the current path between the inner wall and the outer wall while the molten metal is passing through the passage and for detecting voltage changes resulting from the passage through the passage of the suspended particulates.

The accompanying drawing is a sectional side elevation of apparatus according to the invention.

Referring to the drawing, a container comprises a composite wall including an electrically conducting outer wall 10 and an electrically conducting inner wall 12, an electrically insulating barrier 14 including a passage 16 therethrough providing communication between the inside and outside of the container. The outer wall 10 is screw threaded at 18 at its upper end and has an inwardly extending flange 20 at its lower end. The inner wall 12 is internally screw threaded at 22 at its upper end, and has an inwardly extending flange 24 near its lower end. The insulating barrier 14 is held by means of insulating discs 26, 28 between the two flanges 20, 24.

The upper ends of the tubes 10, 12 are held in a block comprising electrically conducting parts 30, 32 separated by an insulating part 34. An axial hole 36 is provided in the block, by means of which a differential pressure can be applied to the container. The conducting region 32 of the block is in electrical contact with the outer tube 10; the conducting region 30 is in electrical contact with the inner tube 12.

An annular space 38 between the inner and outer tubes 10, 12 is filled with densely packed alumina. Alternatively, this space could have been filled with some other electrically insulating heat-conducting material; or it could have been left empty; or a heating element could have been provided to ensure that the contents of the container remained molten.

A deflector 40 is provided at the base of the inner tube and prevents splashing when molten metal is first sucked through the passage 16.

In operation, the container is dipped in molten metal to a level 42. A partial vacuum is applied to the aperture 36, and this causes molten metal to be sucked through the passage 16 and into the container where it is shown as having reached a level 44. When the molten metal in the container reaches a predetermined level, the partial vacuum is replaced by a positive pressure to evacuate the metal to a lower level. This cycle is then repeated as desired. Throughout the cycle, a potential difference is applied across the conducting parts 30 and 32 of the support block. This causes an electric current to flow between them by the only route available, namely via the outer tube 10, the molten metal 42, the passage 16, the molten metal 44, and the inner tube 12. Means (not shown) are provided for measuring the voltage difference between parts 30 and 32 and for detecting voltage changes resulting from the passage through the passage 16 of particulates suspended in the molten metal.

The device of the present invention has several advantages over that described in the aforesaid U.S. Pat. No. 4,555,662:

(a) The electrodes are combined with the container instead of being provided separately.

(b) The container is not made of glass and can therefore be used at higher operating temperatures.

(c) The pressure differential between the inside and outside of the container can be greater.

(d) The disc 14 is a more practical format than a tube, and can be reasonably cheaply made of a variety of refractory materials.

(e) The device can be re-used.

(f) The device is easy to clean. If desired, the flange 20 at the bottom end of the outer tube 10, 12 can be screw threaded to permit easy removal and replacement of the ceramic disc 20, without the need to disturb any insulating material 38 between the inner and outer tubes.

(g) With concentric as opposed to parallel electrodes, magnetic pickup from external sources can be minimized. The general circuit to supply DC current to the electrodes always forms a loop susceptible to magnetic pickup by induction.

The normal way to deal with this situation is to twist the cables together from the battery to the electrodes in order to minimize the total loop area and also to form small cancelling loop areas (even number if possible). It is also necessary to minimize magnetic pickup at the two end loops within the battery and between the two electrodes. Two methods are possible: install compensating loops at each end or surround each end with a material of high permeability (iron, steel, non-metal). The first method involves mechanical problems and difficulties in positioning of the loops (in time and space). The second method is preferred in the case of concentric electrodes. The battery should be surrounded by a material of high permeability. The electrodes (e.g. the tubes 10, 12 and/or the conducting parts 30, 32 of the block 34) may be made of iron or low carbon steel which have good magnetic shielding properties. The outer electrode shields the inner electrode and annular area from the effects of external magnetic fields leading to a reduction in magnetic pickup.

Many features of the present invention are the same as for the apparatus of the aforesaid U.S. Pat No. 4,555,662, and reference to that specification is directed for a fuller discussion of the features described below.

Before use, the interior of the container is flushed with argon gas to avoid as much as possible contamination of the metal by air. The container is then lowered into the molten metal stream, and the interior evacuated. The pump is shut off while tests are under way, so that any electrical noise produced by its electric motor does not hinder electrical signal processing, and so that any pulsations in flow of the evacuating gas are not transmitted to the entering molten metal. The two conductors 30, 32 are connected to a differential amplifier and thence to a logarithmic amplifier, a peak detector and a multi-channel analyser which can also serve as a recorder. The current flow is principally controlled by a ballast resister, and remains sufficiently constant (less than 1% variation) during signal processing. The only changes in voltage that are measured are those arising from the displacement of conducting fluid by particles passing through the passage 16. Each of these particles when sensed produces a record consisting of a positive voltage pulse over and above the steady state value. The magnitude of the transient voltage pulse is related to the equivalent spherical diameter of the particle.

The diameter of the passage 16 can be chosen depending upon the metal under test and the size and nature of the particles to be examined. The diameter will in practice be in the range from 100 to 5000 microns, more usually from about 200 to about 500 microns. For example, the deleterious inclusions commonly found in aluminium are within the range of about 20 to 80 microns in diameter. However, molten steel contains deoxidation products of size in the range about 10 to 80 microns, reoxidation products of size in the range about 100 to 500 microns, and slag particles of as yet unknown size, but many of which are believed to be around 1000 microns.

The electric current required to obtain a useful reading can be very large. The power source used should be capable of delivery a steady current of about 1 to 500A during the period of the test, depending on the diameter of the passage, the resistivity of the metal being tested and the sensitivity desired. In the case of molten aluminium, with an aperture diameter of, say, 300 microns, a preferred range of current is from 1 to 100A, corresponding to a current denisity through the passage of from $1.4 \times 10^7$ to $1.4 \times 10^9 A/m^2$ and a power density of from $5 \times 10^7$ to $5 \times 10^{11} W/m^3$. The current may conveniently be provided by means of a six-volt lead acid battery and an appropriate ballast resister, to provide smooth noise-free power delivery.

While the apparatus of this invention is useful in principle for measuring suspended particulates in any molten metal, it is likely to find principal application in the aluminium and iron/steel industries. Clearly, the tubes 10, 12, the refractory disc 14 and the insulating discs 26, 28 must be made of materials which are resistant to the molten metal. For example, when the molten metal to be sampled is aluminium, the tubes 10, 12 may be made of high carbon steel, or grey cast iron, or of titanium; the refractory disc 14 may be made of borosilicate glass, boron nitride or silicon-carbide; and the insulating discs 26, 28 of aluminosilicate material. The thickness of the refractory disc 14 is not critical, but the passage 16 should preferably be shaped so as to avoid turbulence of molten metal flowing through it, for turbulence perturbs the smooth voltage difference across conductors 30, 32 and obscures the effect of suspended particulates.

It has also been found advantageous to pre-condition a newly-formed passage before a test is performed by passing an extremely heavy current (two to ten times the normal operating current) in the flow path for a period of a few seconds. It is believed that this pre-conditioning may operate by causing intense local heating and possibly vaporization of the metal in the passage which attacks the surface and rids it of adsorbed gases and small holes, thus ensuring that the metal is in complete contact with the wall of the passage. This operation may also be carried out if, during a tests, it is observed that the base line of the electrical recorder becomes unstable.

I claim:

1. Apparatus for the detection and measurement in a molten metal sample of suspended particulates comprising a container defined by a composite wall and an electrically insulating barrier (14), the composite wall including an electrically conducting outer wall (10) and an electrically conducting inner wall (12), the inner wall and outer wall being electrically insulated from one another, and the electrically insulating barrier (14) including a passage (16) of predetermined size therethrough providing communication between the inside and outside of the container, means for causing a sample of molten metal to pass through the passage into (or out of) the container so that molten metal in the container is in electrical contact with the inner wall and molten metal ouside the container is in electrical contact with the outer wall, establishing a current path from the inner wall through the passage to the outer wall, and means connected to the inner wall and the outer wall for passing an electrical current along the current path while the molten metal is passing through the passage and for detecting voltage changes resulting from the passage through the passage of the suspended particulates.

2. Apparatus as claimed in claim 1, wherein the electrically insulating barrier is a disc of refractory material positioned at the bottom of the container.

3. Apparatus as claimed in claim 1, including means for applying a differential pressure to the interior of the container.

4. Apparatus as claimed in claim 1, wherein the inner wall and the outer wall define a space between them.

5. Apparatus as claimed in claim 4, wherein the space is filled with refractory electrically and thermally insulating material.

6. A method for the detection and measurement in a molten metal sample of suspended particulates comprising providing a container having a composite wall including an electrically conducting outer wall and an electrically conducting inner wall, the inner wall and outer wall being electrically insulated from one another, and an electrically insulating barrier including a passage of predetermined size therethrough providing communication between the inside and outside of the container, causing a sample of molten metal to pass through the passage into (or out of) the container so that molten metal in the container is in electrical contact with the inner wall and molten metal outside the container is in electrical contact with the outer wall, establishing a current path from the inner wall through the passage to the outer wall, and passing an electric current along the current path between the inner wall and the outer wall while the molten metal is passing through the passage and detecting voltage changes resulting from the passage through the passage of the suspended particulates.

7. A method as claimed in claim 6, wherein a differential pressure is applied to the interior of the container to cause the sample of molten metal to pass into (or out of) the container.

8. Apparatus as claimed in claim 2, wherein the outer wall (10) has an inwardly extending flange (20) at its lower end, the inner wall (12) has an inwardly extending flange (24) near its lower end, the insulating barrier (14) being held by means of insulating disks (26, 28) between the two flanges, and the flange (20) being screw-threaded to the outer wall to permit easy removal and replacement of the insulating barrier.

* * * * *